United States Patent [19]

Whittle

[11] Patent Number: 4,812,483

[45] Date of Patent: Mar. 14, 1989

[54] INSECTICIDAL ALKENES

[75] Inventor: Alan J. Whittle, Aldershot, England

[73] Assignee: Imperial Chemical Industries PLC, London, England

[21] Appl. No.: 939,778

[22] Filed: Dec. 9, 1986

[30] Foreign Application Priority Data

Dec. 23, 1985 [GB] United Kingdom ............... 8531636
Aug. 6, 1986 [GB] United Kingdom ............... 8619235

[51] Int. Cl.$^4$ .......................................... C07C 43/215
[52] U.S. Cl. ................................. 514/721; 568/636; 568/637; 568/659; 568/661
[58] Field of Search ............... 568/636, 637, 659, 661; 514/721

[56] References Cited

U.S. PATENT DOCUMENTS

| 4,123,556 | 10/1978 | Karrer | 568/636 |
| 4,141,921 | 2/1979 | Karrer | 568/636 |
| 4,397,864 | 8/1983 | Nakatani et al. | 514/461 |
| 4,570,005 | 2/1986 | Nakatani et al. | 568/636 |

FOREIGN PATENT DOCUMENTS 0094085 11/1983 European Pat. Off. .
2342953 9/1977 France .
2085006 4/1982 United Kingdom .

OTHER PUBLICATIONS

Solomons, *Organic Chemistry*, 2nd Edition, 1980, p. 717.
Tetrahedron Letters, No. 49, pp. 4257–4260 (Dec. 1977).
Abstract, 6th IUPAC Conference (Aug. 10–15, 1986).

*Primary Examiner*—Mary C. Lee
*Assistant Examiner*—Zinna Northington
*Attorney, Agent, or Firm*—Cushman, Darby & Cushman

[57] ABSTRACT

A compound of formula:

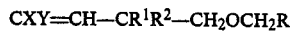

$$CXY=CH-CR^1R^2-CH_2OCH_2R$$

wherein X and Y are each selected from hydrogen and halogen, $R^1$ and $R^2$ are each lower alkyl of up to four carbon atoms, or together with the adjacent carbon atom form a cycloalkyl group of up to six carbon atoms, and R represents a phenoxy- or benzyl-substituted phenyl group which may optionally be substituted with fluorine. The compounds are useful for combating insect pests.

5 Claims, No Drawings

INSECTICIDAL ALKENES

This invention relates to novel ethers useful as insecticides and their preparation, to insecticidal compositions thereof and to methods of combating and controlling insect pests therewith.

In a first aspect the invention provides compounds of formula:

$$CXY=CH-CR^1R^2-CH_2OCH_2R \qquad (I)$$

wherein X and Y are each selected from hydrogen and halogen, $R^1$ and $R^2$ are each lower alkyl of up to four carbon atoms or together with the adjacent carbon atom form a cycloalkane groups of up to six carbon atoms and R represents a phenoxy- or benzyl- substituted phenyl or pyridyl group which may also be substituted by fluorine.

Preferably X and Y are each selected from hydrogen, fluoro, chloro and bromo, $R^1$ and $R^2$ are methyl or ethyl or together represent the dimethylene group and R is a group of formula:

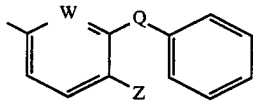

where W represents nitrogen or a carbon atom bearing a hydrogen atom, Z is hydrogen or fluoro, and Q is oxygen or methlene.

Particular compounds according to the invention are set out in Table I below wherein the meanings of X, Y and $R^1$ and $R^2$, and R are given. R is defined as a group $E^1$ to $E^4$ wherein $E^1$ to $E^4$ are as follows:

$E^1$ = 3-phenoxyphenyl
$E^2$ = 3-phenoxy-4-fluorophenyl
$E^3$ = 6-phenoxypyrid-2-yl
$E^4$ = 3-benzyl-4-fluorophenyl.

TABLE I

| COMPOUND NO | X | Y | $R^1,R^2$ | R |
|---|---|---|---|---|
| 1 | Cl | Cl | $CH_3,CH_3$ | $E^2$ |
| 2 | H | H | $CH_3,CH_3$ | $E^1$ |
| 3 | Br | Br | $CH_3,CH_3$ | $E^1$ |
| 4 | Cl | Cl | $CH_3,CH_3$ | $E^1$ |
| 5 | H | H | $CH_3,CH_3$ | $E^2$ |
| 6 | H | H | $CH_2-CH_2$ | $E^1$ |
| 7 | H | Br | $CH_3,CH_3$ | $E^1$ |
| 8 | H | H | $CH_3,C_2H_5$ | $E^1$ |
| 9 | Cl | Cl | $CH_2-CH_2$ | $E^1$ |
| 10 | Cl | H | $CH_3,CH_3$ | $E^1$ |
| 11 | F | Cl | $CH_3,CH_3$ | $E^1$ |
| 12 | H | H | $CH_3,CH_3$ | $E^3$ |
| 13 | Cl | Cl | $CH_3,CH_3$ | $E^3$ |
| 14 | H | H | $CH_3,CH_3$ | $E^4$ |
| 15 | F | F | $CH_3,CH_3$ | $E^2$ |
| 16 | F | F | $CH_3,CH_3$ | $E^3$ |
| 17 | F | F | $CH_3,CH_3$ | $E^1$ |
| 18 | F | F | $CH_3,CH_3$ | $E^4$ |
| 19 | F | Cl | $CH_3,CH_3$ | $E^3$ |
| 20 | Cl | Cl | $CH_3,CH_3$ | $E^3$ |

In the compounds according to the invention geometric isomerism will arise where X and Y are not identical, and the scope of the invention includes the resultant E and Z isomers as well as mixtures thereof. Similarly where $R^1$ and $R^2$ are not identical the compounds will exist as optically active isomers having (R) and (S) configurations and the scope of the invention includes such isomers in isolation as well as mixtures thereof, including racemic mixtures.

The compounds of the invention may be prepared by reacting an aldehyde of formula:

$$OCH-CR^1R^2-CH_2OCH_2R$$

wherein $R^1$, $R^2$ and R are as defined hereinabove, with a triphenylphosphonium salt of formula:

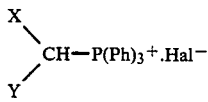

where X and Y are as defined hereinabove and $Hal^-$ represent a halide ion, in the presence of a base e.g., an alkali metal alkoxide, under the conditions of the Wittig reaction.

In cases where X and Y are both halogen atoms their reactions with the phosphonium salt may be replaced by reaction with a carbon tetrahalide and triphenylphosphine, or with carbon tetrahalide and hexamethylphosphorous triamide.

The compounds of formula:

$$OCH-CR^1R^2-CH_2OCH_2R^4$$

which have not previously been described may be prepared by oxidation of novel compounds of formula:

$$HOCH_2-CR^1R^2-CH_2OCH_2R$$

wherein $R^1$, $R^2$ and R are as defined hereinabove. A suitable oxidising agent is pyridinium chlorochromate.

$$HOCH_2-CR^1R^2-CH_2OCH_2R^4$$

useful as intermediates heein can be prepared by reacting a benzyl halide of formula R-Q (where Q is halo, preferably chloro or bromo) with a diol of formula:

$$HOCH_2-CR^1R^2-CH_2OH$$

in the presence of a base, e.g., sodium hydride.

The following Scheme illustrates the preparation of 1,1-dichloro-3,3-dimethyl-4-(3-phenoxy-4-fluorobenzyloxy)-but-1-ene.

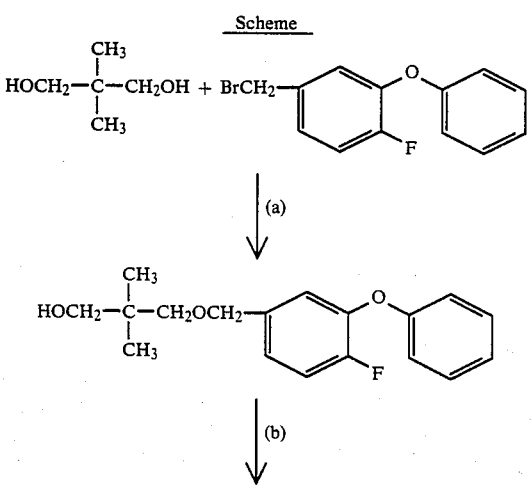

-continued
Scheme

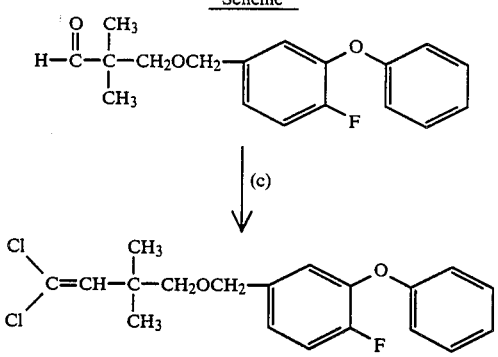

(a) Sodium hydride/tetrahydrofuran
(b) Pyridinium chlorochromate/dichloromethane
(c) Carbon tetrachloride/triphenyl phosphine Further details of the processes for preparing the compounds of the invention may be ascertained from the specific Examples hereinafter.

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence at the locus of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:
(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphosmethyl, fenitrothion or diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemyins, for example such as abamectin, avermectin, and milbemycin;

(g) Hormones such as juvenile hormone, juvabione, or ecdysones;

(h) Pheromones;

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect pecies/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the composition include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
Aonidiella spp. (scale insects)
Trialeuroides spp. (white flies)
*Blattella germanica* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaparvata lugens* (plant hoppers)

The compounds of formula I and compositions comprising them have shown themselves to be particularly useful in controlling pests of maize and rice such as Chilo (stem borers) as well as lepidopteran pests of cotton, for example Spodoptera spp. and Heliothis spp.

Although all of the invention compounds of formula I show insecticidal properties in the tests described hereinafter in the Examples they are not all equally effective at the particular rates tested to all of the test species.

Some of the compounds are particularly useful for the control of insect pests of rice because they show high levels of activity against rice pests such as Chilo sp. and Nilaparvata sp. at rates which are not toxic to fish, thus enabling their use in paddy rice where fish are cultivated in the paddy.

The various aspects of the invention are illustrated in the following Examples.

In the Examples, Gas Liquid Chromatography (GLC) retention times were determined on a Hewlett Packard 5890 Gas Chromatograph, using a Chromopak C.P Sil 5 C.B. column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise stated. $^{19}$F NMR spectrometry was performed on a Joel FX90Q spectrometer at a frequency of 84.26 MHz.

EXAMPLE 1

This Example illustrates the preparation of 1,1-di(hydroxymethyl)cyclopropane.

A solution of diethyl-1,1-cyclopropane-dicarboxylate (10 g) in tetrahydrofuran (25 cm$^3$) was added dropwise to a stirred suspension of lithium aluminium hydride (2.15 g) in tetrahydrofuran (75 cm$^3$) whilst the reaction temperature was maintained below 20° C. When the addition was complete the mixture was allowed to warm to the ambient temperature (ca. 25° C.), and allowed to stir for a further 2 hours. A saturated solution of sodium potassium tartrate was then added carefully to the reaction mixture, which was then allowed to stand for 18 hours. The mixture was extracted into ethylacetate several times and the combined extracts dried over anhydrous magnesium sulphate. Removal of the solvent by evaporation gave 1,1-di(hydroxymethyl)cyclopropane (3 g).

$^1$H nmr (CDCl$_3$) ppm: 0.5 (s,4H); 2.7 (broad s,2H); and 3.6 (s,4H).

Infra red (liquid film): 3400 and 1020 cm$^{-1}$.

EXAMPLE 2

This Example illustrates the preparation of 1-hydroxymethyl-1-(3-phenoxybenzyloxymethyl)cyclopropane.

A solution of 1,1-dihydroxymethylcyclopropane (3 g) in tetrahydrofuran (20 cm$^3$) was added dropwise to a suspension of sodium hydride (0.35 g) in tetrahydrofuran (30 cm$^3$). After effervescence has ceased, tetrabutylammonium iodide (1 g) was added to the grey suspension followed by a solution of 3-phenoxybenzyl bromide (3.88 g) in tetrahydrofuran (15 cm$^3$) at the ambient temperature and the mixture stirred for a further 2 hours. The mixture was poured into water and extracted with ethylacetate. The extracts were combined, dried over magnesium sulphate and concentrated by evaporation of the solvent, and the residual oil purified by column chromatography using a silica gel column eluting first with dichloromethane, followed then by ethylacetate, to give 1-hydroxymethyl-1-(3-phenoxybenzyloxymethyl)cyclopropane (1.7 g).

$^1$H nmr (CDCl$_3$) ppm: 0.5 (s,4H); 2.45 (broad s,1H); 3.4 (s,2H); 3.5 (s,2H); 4.5 (s,2H); and 6.9–7.5 (m,9H).

Infra red (liquid film): 3450, 1575, 1475, 1245 and 680 cm$^{-1}$ (major peaks only).

EXAMPLE 3

This Example illustrates the preparation of 2,2-dimethyl-3-(3-phenoxybenzyloxy)propan-1-ol.

A solution of 2,2-dimethylpropan-1,3-diol (15.6 g) in tetrahydrofuran (100 cm$^3$) was added in small aliquots to a stirred suspension of sodium hydride (1.8 g) in tetrahydrofuran (100 cm$^3$) with cooling. After effervescence had ceased, tetra-n-butylammonium iodide (5 g) was added to the resultant grey suspension followed by addition of solution of 3-phenoxybenzyl bromide (19.7 g) in dry tetrahydrofuran (100 cm$^3$) at the ambient temperature (ca. 25° C.), and the mixture stirred for a further 2 hours. The mixture was poured into water and extracted with ethyl acetate. The extracts were combined, dried over anyhydrous magnesium sulphate and concentrated by evaporation of the solvent. The residual oil was identified as a mixture of 2,2-dimethyl-3-(3-phenoxybenzyloxy)propan-1-ol and 2,2-dimethylpropan-1,3-diol by nmr and infra red spectroscopic examination.

$^1$H nmr (CDCl$_3$) ppm: 0.9 (s,6H); 2.4 (broad s,1H); 3.3 (s,2H); 3.5 (broad d,1H); 4.5 (s,2H); and 6.8–7.5 (m,9H).

Infra red (liquid film): 3340, 1585, 1490 and 1255 cm$^{-1}$.

EXAMPLE 4

This Example illustrates the preparation of 2-ethyl-2methyl-3-(3-phenoxybenzyloxy)propan-1-ol.

2-Ethyl-2-methylpropan-1,3-diol (9.44 g) was reacted according to the procedure laid out in Example 2 to give the crude product as an impure oil. Distillation through a kugelrohr apparatus give two fractions. The first being by gas chromatography the desired compound whilst the second fraction (B. pt. 200° C./0.03 mmHg) was the desired 2-ethyl-2-methyl-3-(3-phenoxybenzyloxy)propan-1-ol (3.6 g).

$^1$H nmr (CDCl$_3$) ppm : 0.8 (m,6H); 1.4 (m,2H); 2.5 (broad s,1H); 3.4 (s,2H); 3.5 (broad s,2H); 4.5 (s,2H); and 6.9–7.5 (m,9H).

Infra red (liquid film): 3450, 1590, 1490, 1260, 1220, and 695 cm$^{-1}$ (major peaks only).

EXAMPLE 5

This Example illustrates the preparation of 2,2-dimethyl-3-(4-fluoro-3-phenoxybenzyloxy)propan-1-ol.

A solution of 2,2-dimethylpropan-1,3-diol (5.2 g) in tetrahydrofuran (35 cm$^3$) was added in a small aliquots to a stirred suspension of sodium hydride (0.6 g) in tetrahydrofuran (35 cm$^3$) with cooling. After effervescence had ceased tetrabutylammonium iodide (1.7 g) was added to the resultant grey suspension followed by addition of a solution of 4-fluoro-3-phenoxybenzyl bromide (7.1 g) in dry tetrahydrofuran (30 cm$^3$) at the ambient temperature (ca. 25° C.), and the mixture stirred for a further 2 hours. The mixture was poured into water and extracted with ethyl acetate. The extracts were combined, dried over anhydrous magnesium sulphate and concentrated by evaporation of the solvent and the residual oil identified as a mixture of 2,2-dimethyl-3-(4-fluoro-3-phenoxybenzyloxy)propan-1-ol and some unreacted 2,2-dimethylpropan-1,3-diol by nmr and infra red spectroscopic examination.

$^1$H nmr (CDCl$_3$) ppm: 0.9 (s,6H); 2.2 (broad s,1H); 3.3 (s,2H); 3.5 (s,2H); 4.4 (s,2H); and 6.9–7.4 (m,8H).

Infra red (liquid film): 3400, 1595, 1515, 1280, 1215 cm$^{-1}$ (major peaks only).

EXAMPLE 6

This Example illustrates the preparation of 2,2-dimethyl-3-(3-phenoxybenzyloxy)propan-1-al.

A solution of 2,2-dimethyl-3-(3-phenoxybenzyloxy)-propan-1-ol (15 g) in dry dichloromethane (50 cm$^3$) was added dropwise to a stirred suspension of pyridinium chlorochromate (18.75 g) in dichloromethane (100 cm$^3$) whilst the reaction temperature was maintained within the range 0°–5° C. When the addition was complete, the mixture was allowed to warm to the ambient temperature (ca. 25° C.) over a period of 2 hours. After the reaction mixture had been diluted with diethyl ether, the ethereal layer was decanted and filtered through celite. The solvent was removed by evaporation and the residual oil purified by column chromatography using a silica gel column and eluting with dichloromethane as eluent, to yield 2,2-dimethyl-3-(3-phenoxybenzyloxy)-propane-1-al (7.2 g) as an orange oil.

$^1$H nmr (CDCl$_3$) ppm : 1.1 (s,6H); 3.45 (s,2H); 4.5 (s,2H); 6.8–7.4 (m,9H); and 9.55 (s,1H).

Infra red (liquid film): 1735, 1590, 1490, 1445, 1250, 1215, 1100 and 690 cm$^{-1}$.

EXAMPLE 7

This Example illustrates the preparation of 2-ethyl-2-methyl-3-(3-phenoxybenzyloxy)propan-1-al.

2-Ethyl-2-methyl-3-(3-phenoxybenzyloxy)propan-1-ol (3.6 g) was reacted according to the procedure in Example 6. The crude product was distilled through a kugelrohr apparatus to give 2-ethyl-2-methyl-3-(3-phenoxybenzyloxy)- propan-1-al (2.35 g) (BPt 170° C./0.07 mm Hg).

$^1$H nmr (CDCl$_3$) ppm: 0.8 (t,3H); 1.05 (s,3H); 1.55 (m,2H); 3.4 (d,1H); 3.5 (d,1H); 4.45 (s,2H); 6.9–7.4 (m,9H); and 9.5 (s,1H).

Infra red (liquid film): 1730, 1590, 1490, 1260, 1220, and 695 cm$^{-1}$.

EXAMPLE 8

This Example illustrates the preparation of 1-formyl-1-(3-phenoxybenzyloxymethyl)cyclopropane.

A solution of dry dimethyl sulphoxide (0.87 g) in dichloromethane (12 cm$^3$) was added dropwise to a stirred solution of oxalyl chloride (0.75 g) in dichloromethane (12 cm$^3$) maintained at $-70°$ C. After a period of five minutes had elapsed, a solution of 2-cyclopropyl-3-(3-phenoxybenzyloxy)propane-1-ol (1.45 g) in dichloromethane (6 cm$^3$) was added dropwise, followed by triethylamine (2.3 g) five minutes later. When the addition was complete the mixture was allowed to warm to the ambient temperature over a period of 2 hours. The reaction mixture was poured into water, and extracted with diethyl ether. The extracts were combined, dried over anhydrous magnesium sulphate and concentrated by evaporation of the solvent. The residual oil (1.5 g) was purified by column chromatography using a silica gel column and eluting with dichloromethane to yield 1-formyl-1-(3-phenoxybenzyloxymethyl)cyclopropane (1 g).

$^1$H nmr (CDCl$_3$) ppm: 1.2 (m,4H); 3.7 (s,2H); 4.5 (s,2H); 6.9–7.4 (m,9H); and 9.0 (s,1H).

Infra red (liquid film): 1715, 1590, 1490, 1260, 1220, and 1100 cm$^{-1}$.

EXAMPLE 9

This Example illustrates the preparation of 2,2-dimethyl-3-(4-fluoro-3-phenoxybenzyloxy)propan-1-al.

A solution of 2,2-dimethyl-3-(4-fluoro-3-phenoxybenzyloxy)propan-1-ol (5.0 g) in dichloromethane (30 cm$^3$) was added dropwise to a stirred suspension of pyridinium chlorochromate (6.77 g) in dichloromethane (20 cm$^3$) whilst the reaction temperature was maintained within the range 0°–5° C. When the addition was complete the mixture was allowed to warm to the ambient temperature over a period of 2 hours. The solvent was removed and the residual oil (3.0 g) purified by column chromatography using a silica gel column and eluting with a 10:1 (by volume) mixture mixture of petroleum ether (boiling range 40°–60°) and diethyl ether to yield 2,2-dimethyl-3-(4-fluoro-3-phenoxybenzyloxy)propan-1-al (1.5 g) as a yellow oil.

$^1$H nmr (CDCl$_3$) ppm: 1.1 (s,6H); 3.5 (s,2H); 4.5 (s,2H); 7.0–7.5 (m,8H); 9.6 (s,1H).

Infra red (liquid film) : 1735, 1590, 1510, 1490, 1280, 1210 cm$^{-1}$ (major peaks only).

EXAMPLE 10

This Example illustrates the preparation of 2-chloromethyl-6-phenoxypyridine.

Triethylamine (2.27 cm$^3$) was added portionwise to a stirred solution of 2-hydroxymethyl-6-phenoxypyridine (3 g), para-toluenesulphonyl chloride (3.7 g), and 4-dimethylaminopyridine (1.17 g) in dichloromethane (30 cm$^3$), whilst the reaction mixture was maintained at the ambient temperature (ca 22° C.) under an atmosphere of nitrogen. After a period of four hours, the reaction mixture was poured into diethyl ether, and washed sequentially with saturated aqueous sodium bicarbonate, water and brine. The organic layer was then dried, and after removal of the solvent by evaporation under reduced pressure, the crude crude product was subjected to column chromatography on silica gel using dichloromethane as eluent to give 2-chloromethyl-6-phenoxypyridine (2.05 g).

$^1$H nmr (CDCl$_3$) ppm: 4.55 (s,2H); 6.75 (d,1H); 7.2 (m, 4H); 7.4 (m,2H); 7.7 (t,1H).

Infra red (liquid film): 2980, 1595, 1575, and 1445 cm$^{-1}$.

GLC retention time: 4.27 minutes.

EXAMPLE 11

This Example illustrates the preparation of 2,2-dimethyl-3-(6-phenoxypyrid-2-yl)methoxypropan-1-ol.

2,2-Dimethylpropan-1,3-diol was reacted with 2-chloromethyl-6-phenoxypyridine according to the procedure set out in Example 3, using dimethylformamide as solvent.

The crude product was purified by column chromatography on silica gel using petrol ether (boiling range 40°–60° C.) containing 40% by volume diethyl ether as eluent, to give 2,2-dimethyl-3-(6-phenoxypyrid-2-yl)methoxypropan-1-ol as a red oil.

$^1$H nmr (CDCl$_3$) (ppm): 0.95 (s,6H); 3.4 (s,2H); 3.5 (s,2H); 4.5 (s,2H); 6.65 (d,1H); 7.15 (m,4H); 7.4 (t,2H); 7.65 (t,1H).

IR (liquid film): 3400, 2960, 2870, 1598, 1580 and 1440 cm$^{-1}$.

GLC retention time: 7.29 minutes.

EXAMPLE 12

This Example illustrates the preparation of 2,2-dimethyl-3-(6-phenoxypyrid-2-yl)methoxypropan-1-al.

2,2-Dimethyl-3-(6-phenoxypyridin-2-yl)methoxypropan-1-ol was reacted according to the procedure set out in Example 6. The crude product was subject to column chromatography on silica gel using petroleum ether (boiling range 40°–60° C.) containing 20% by volume diethylether as eluent, to give 2,2-dimethyl-3-(6-phenoxypyridin-2-yl)methoxypropan-1-al.

$^1$H nmr (CDCl$_3$) ppm: 1.1 (s,6H); 3.55 (s,2H); 4.5 (s,2H); 6.7 (d,1H); 7.0–7.2 (m,4H); 7.4 (t,2H); 7.65 (t, 1H); 9.6 (s,1H);

IR (liquid film): 2980, 2880, 1730, 1598, 1580 and 1440 cm$^{-1}$.

GLC retention time: 6.91 minutes.

EXAMPLE 13

This Example illustrates the stages in the preparation of 3-benzyl-4-fluorobenzyl alcohol.

Stage 1: Preparation of 3-bromo-4-fluorobenzaldehyde.

A solution of 4-fluorobenzaldehyde (49.6 g) in dry dichloromethane (20 cm$^3$) was added to a cooled (0° C.) suspension of powdered aluminium trichloride (90.4 g) in dry dichloromethane (100 cm$^3$). Bromine (70.4 g) was added, and the mixture heated at the reflux temperature for 16 hours. After cooling, the reaction mixture was carefully poured onto ice and extracted with dichloromethane. The combined organic layers were washed with saturated sodium metabisulphite solution, water and brine, then dried over anhydrous magnesium sulphate. Evaporation of the solvent under reduced pressure gave a dark red oil, which was purified by distillation under reduced pressure, using a 4″ Vigreux column to give 3-bromo-4-fluorobenzaldehyde (45.7 g) as an oil, boiling point 85°–108° C. at 8 mmHg.

Stage 2: Preparation of 2-(3-bromo-4-fluorophenyl)-1,3-dioxolane.

A mixture of 3-bromo-4-fluorobenzaldehyde (45.7 g), ethylene glycol (27.39 g), p-toluenesulphonic acid (0.225 g) and dry toluene (110 cm$^3$) was heated at the reflux temperature under a Dean and Stark trap. After 4.5 hours, approximately 12 cm³ of water had collected in the trap, and analysis of the reaction mixture by gas liquid chromatography indicated that no starting aldehyde was present. The mixture was sodium bicarbonate solution and brine, and dried over anhydrous magnesium sulphate. Evaporation of the solvent under reduced pressure gave a yellow oil, which was purified by distillation under reduced pressure to give 2-(3-bromo-4-fluorophenyl)-1,3-dioxolane (43.56 g), boiling point 68°-106° C. at 0.004 mmHg.

90 MHz 1H NMR (CDCl₃) (ppm): 4.1 (4H,m); 5.8 (1H,s); 7.0-7.7 (3H,m).

Stage 3: Preparation of 2-(3-benzyl-4-fluorophenyl)-1,3-dioxolane.

This compound was prepared by a method analogous to that reported by Minato et al in Tetrahedron Letters, 21, 845, 1980.

Benzyl bromide (2.77 g) was added in one addition to a suspension of activated zinc powder (2.1 g) in dry tetrahydrofuran (20 cm³) under an atmosphere of nitrogen.

The reaction mixture was sonicated for 2 hours, allowed to stand for 30 minutes and carefully filtered under an atmosphere of nitrogen. The filtered solution was then added to a mixture of 2-(3-bromo-4-fluorophenyl)-1,3-dioxolane (1 g) and palladium (O) tetakis triphenylphosphine (0.05 g) in dry tetrahydrofuran (10 cm³) under an atmosphere of nitrogen. The stirred mixture was heated at the reflux temperature for 48 hours, at which time analysis by gas liquid chromatography showed no trace of starting material. The reaction mixture was cooled and poured into diethyl ether. The organic layer was separated, and washed with ammonium chloride solution, water and brine, then dried over anhydrous magnesium sulphate. Evaporation of the solvent under reduced pressure gave a yellow oil which was purified by column chromatography on a silica gel support, using petroleum ether (boiling range 40°-60° C.) containing diethyl ether (progressively increased from 10% to 20% by volume) as eluent to give 2-(3-benzyl-4-fluorophenyl)-1,3-dioxolane (0.7 g). The product was used without further purification.

60 HMz 1H NMR (CDCl₃) (ppm): 4.0 (6H,m); 5.7 (1H,s); 6.8-7.5 (8H,m).

Stage 4: Preparation of 3-benzyl-4-fluorobenzaldehyde.

A mixture of 2-(3-benzyl-4-fluorophenyl)-1,3-dioxolane (0.7 h) acetone (10 cm³), water (1 cm³) and concentrated sulphuric acid (5 drops) was stirred for 16 hours. The reaction mixture was poured into diethyl ether and the organic layer washed with sodium bicarbonate solution, water and brine, then dried over anhydrous magnesium sulphate. Evaporation of the solvents under reduced pressure gave 3-benzyl-4-fluorobenzaldehyde (0.59 g), which was used without further purification.

¹H NMR (CDCl₃O (ppm): 4.10 (2H,s); 7.20 (6H,m); 7.75 (2H,m); 9.90 (1H,s).

IR (liquid film): 1700 cm⁻¹ (C=O).

Stage 5: Preparation of 3-benzyl-4-fluorobenzyl alcohol.

A solution of 3-benzyl-4-fluorobenzaldehyde (5 g) in methanol (75 cm³) was cooled to 0° C. Sodium borohydride (1.34 g) was added in portions, and the mixture stirred for 1 hour. The reaction mixure was then poured cautiously into a mixture of water and diethyl ether, and the organic layer was separated, washed with water and brine, and dried over anhydrous magnesium sulphate. Evaporation of the solvents under reduced pressure gave a pale yellow oil which was purified by distillation in a kugelrohr apparatus to give 3-benzyl-4-fluorobenzyl alcohol (4.0 g).

Boiling point: 120° C. at 0.02 mmHg.

¹H NMR (CDCl₃) (ppm): 1.7 (1H,broad s); 4.0 (2H,s); 4.6 (2H,s); 7.0-7.3 (8H,m).

IR (liquid film): 3600-3100 cm⁻¹ (OH).

EXAMPLE 14

This Example illustrates the preparation of 3-benzyl-4-fluorobenzyl bromide.

Triphenylphosphine (2.91 g) was added portionwise over two minutes to a stirred solution of 3-benzyl-4-fluorobenzylalcohol (2 g) and 1,2-dibromotetrachloroethane (3.61 g) in dry diethyl ether (60 cm³), whilst the temperature was maintained at 0° C. After a period of ten minutes, the reaction mixture was filtered, and the solvent evaporated under reduced pressure.

The residue was passed through a small plug of silica gel using petroleum ether (boiling range 40°-60° C.) containing diethyl ether (10% by volume) as eluent to give 3-benzyl-4-fluorobenzyl bromide as a slightly impure oil.

¹H nmr (CDCl₃) (ppm): 4.0 (s,2H); 4.4 (s,2H); 6.8-7.5 (m,8H).

GLC retention time: 5.87 minutes.

EXAMPLE 15

This Example illustrates the preparation of 2,2-dimethyl-2-(3-benzyl-4-fluorobenzyloxy)propan-1-ol.

A solution of 2,2-dimethylpropan-1,3-diol (2.18 g) in tetrahydrofuaan (15 cm³) was added in small aliquots to a stirred suspension of sodium hydride (0.5 g) in tetrahydrofuran (15 cm³).

The stirred suspension was gently heated to 45° C. until effervescence had ceased (ca 20 minutes). After cooling to 0° C., a catalytic amount of tetra-n-butyl ammonium iodide was added, followed by a solution of 3-benzyl-4-fluorobenzyl bromide (2.93 g) in tetrahydrofuran (10 cm³). The reaction mixture was then warmed to 45° C. for 1 hour, and then left to stand at the ambient temperature (ca 25° C.) for 60 hours.

The reaction mixture was poured into water and extracted with diethyl ether. The extracts were combined, dried over anhydrous magnesium sulphate and concentrated by evaporation of the solvent. The residual oil was then oxidised as illustrated in the following Example.

EXAMPLE 16

This Example illustrates the preparation of 2,2-dimethyl-3-(3-benzyl-4-fluorobenzyloxy)-propan-1-al.

A solution of 2,2-dimethyl-3-(3-benzyl-4-fluorobenzyloxy)-propan-1-ol (from the previous Example) in dichloromethane (15 cm³) was added dropwise to a stirred suspension of pyridinium chlorochromate (5.13 g) in dichloromethane (40 cm³) whilst the reaction temperature was maintained within the range 0°-5° C. When the addition was complete the mixture was allowed to warm to the ambient temperature (ca 25° C.) over a period of two hours, and left to stir for 14 hours. Diethyl ether was then added to the reaction mixture, and the whole was flushed through a plug of silica gel using diethyl ether as eluent. Evaporation of the solvent under reduced pressure gave a green oil which was subjected to column chromatography through silica gel using petroleum ether (boiling range 40°-60° C.) containing diethyl ether (10% by volume) as eluent, to give 2,2-dimethyl-3-(3-benzyl-4-fluorobenzyloxy)propan-1-al (1.40 g).

$^1$H nmr (CDCl$_3$) (ppm): 1.05 (s, 6H); 3.39 (s,2H); 3.99 (s,2H); 4.40 (s,2H); 6.95–7.3 (m,8H); 9.52 (s,1H);

Infra Red (liquid film): 2880, 1732, 1608, 1508, 1250, and 1105 cm$^{-1}$.

GLC retention time: 7.84 minutes.

EXAMPLE 17

This Example illustrates the preparation of 3,3-dimethyl-4-(4-fluoro-3-phenoxybenzyloxy)but-1-ene (Compound No 5).

Methyltriphenylphosphonium bromide (3 g) was added in portions to a stirred suspension of potassium t-butoxide (0.92 g) in dry diethyl ether (25 cm$^3$), and the resultant mixture stirred for 30 minutes after which a solution of 2,2-dimethyl-3-(4-fluoro-3-phenoxybenzyloxy)propan-1-al (2.5 g) in diethyl ether (25 cm$^3$) was added to the mixture.

An exotherm was noted, and after 10 minutes the mixture was poured into water, and extracted with ethylacetate, the extracts combined, washed with water and dried over anhydrous magnesium sulphate, and concentrated by evaporation of the solvent to yield a yellow oil. This was flash chromatographed on a silica gel column with dichloromethane as eluent to yield 2,2-dimethyl-1-(4-fluoro-3-phenoxybenzyloxy)but-3-ene (1.6 g) as a pale yellow liquid.

$^1$H nmr (CDCl$_3$) ppm: 1.0 (s,6H); 3.2 (s,2H); 4.4 (s,2H); 4.95 (m,2H); 5.8 (dd,1H); and 7.0–7.4 (m,8H).

Infra Red (liquid film): 2980, 1590, 1515, 1490, 1285, 1215, and 690 cm$^{-1}$.

EXAMPLE 18

The following compounds were prepared according to the procedure given in Example 17:

(I) 3,3-Dimethyl-4-(3-phenoxybenzyloxy)but-1-ene from 2,2-dimethyl-3-(3-phenoxybenzyloxy)propan-1-al (Kugelrohr boiling point 100° C. at 0.075 mm Hg) (Compound No 2).

$^1$H nmr (CDCl$_3$) ppm: 1.0 (s,6H); 3.2 (s,2H); 4.5 (s,2H); 4.9–5.15 (m, 2H); 5.85 (dd, 1H); and 6.9–7.5 (m, 9H).

Infra Red (liquid film): 1580, 1480, 1440, 1245, 1210, 1100 and 685 cm$^{-1}$.

(II) 1-(3-phenoxybenzyloxymethyl)-1-vinylcyclopropane from 1-formyl-1-(3-phenoxybezyloxymethyl)-cyclopropane (Compound No 6).

$^1$H nmr (CDCl$_3$) ppm: 0.7 (s,4H); 3.4 (s,2H); 4.5 (s,2H); 4.95–5.1 (m,2H); 5.65 (dd, 1H), and 6.9–7.4 (m, 9H).

Infra Red (liquid film): 1590, 1490, 1260, 1220 and 695 cm$^{-1}$.

(III) 3-Ethyl-3-methyl-4(3-phenoxybenzyloxy)but-1-ene from 2-ethyl-2-methyl-3-(3-phenoxybenzyloxy)propan-1-al (Compound No 8).

$^1$H nmr (CDCl$_3$) ppm : 0.8 (t,3H); 1.0 (s,3H); 1.4 (q,2H); 3.2 (s,2H); 4.45 (s,2H); 4.8–5.05 (m,2H); 5.8 (dd, 1H); and 6.9–7.4 (m, 9H).

Infra Red (liquid film): 1590, 1490, 1260, 1110 and 659 cm$^{-1}$.

(IV) 3,3-Dimethyl-4-(6-phenoxypyrid-2-yl)methoxybut-1-ene from 2,2-dimethyl-3-(6-phenoxypyrid-2-yl)methoxypropan-1-al (Compound No 13).

$^1$H nmr (CDCl$_3$) ppm: 1.05 (s,6H); 3.3 (s,2H); 4.5 (s,2H); 5.0 (m,2H); 5.9 (dd,1H); 6.65 (d,1H); 7.2 (m,4H); 7.4 (t,2H); 7.65 (t,1H).

Infra Red (liquid film): 2960, 1595, 1575 and 1435 cm$^{-1}$.

GLC retention time: 6.42 minutes.

(V) 3,3-Dimethyl-4-(3-benzyl-4-fluorobenzyloxy)but-1-ene from 2,2-dimethyl-3-(3-benzyl-4-fluorobenzyloxy)propan-1-al (Compound No 14).

$^1$H nmr (CDCl$_3$) (ppm): 1.00 (s,6H); 3.14 (s,2H); 3.99 (s,2H); 4.42 (s,2H); 5.0 (m,2H); 5.8 (dd,1H); 6.9–7.35 (m,8H).

Infra Red (liquid film): 2980, 1608, 1505 and 1100 cm$^{-1}$.

GLC retention time: 7.16 minutes.

EXAMPLE 19

This Example illustrates the preparation of 2,2-dimethyl-1-(4-fluoro-3-phenoxybenzyloxy)-4,4-dichlorobut-3-ene (Compound No 1).

A mixture of 2,2-dimethyl-3-(4-fluoro-3-phenoxybenzyloxy)propan-1-al (0.5 g), triphenylphosphine (0.43 g) and carbon tetrachloride (1.0 cm$^3$) was heated at the reflux temperature for 1 hour. After cooling to the ambient temperature the mixture was diluted with petroleum ether (boiling range 40°–60° C.) and the solid component removed by filtration. The filtrate was concentrated by evaporation of the solvent under reduced pressure and the redidual oil subjected to purification by flash chromatography using a silica column eluted with petroleum ether (boiling range 40°–60° C.) containing diethyl ether (10% by volume) as eluent to yield 2,2-dimethyl-1-(4-fluoro-3-phenoxybenzyloxy)-4,4-dichlorbut-3-ene (0.1 g) as a colourless oil.

$^1$H nmr (CDCl$_3$) ppm: 1.2 (s,6H); 3.25 (s,2H); 4.45 (s,2H); 5.95 (s,1H); 7.0–7.4 (m,8H).

Infra Red (liquid film): 1605, 1585, 1505, 1480, 1275, 1205, 1100, 870 cm$^{-1}$.

Mass spectrum (m/e): 370, 368 (m+), 216, 202, 201, 181.

EXAMPLE 20

This Example illustrates the preparation of 2,2-dimethyl-1-(3-phenoxybenzyloxy)-4,4-dichlorobut-3-ene (Compound No 4).

A mixture of 2,2-dimethyl-3-(3-phenoxybenzyloxy)-propan-1-al (0.25 g), triphenylphosphine (0.47 g), zinc dust (0.12 g) and carbon tetrachloride (0.2 cm$^3$) was heated at the relux temperature for one hour. After cooling to the ambient temperature (ca 25° C.) the mixture was diluted with petroleum ether (boiling range 40°–60° C.) and the solid component removed by filtration. The filtrate was concentrated by evaporation of the solvent under reduced pressure, and the residual oil subjected to purification by flash chromatography using a silica gel column eluted with dichloromethane to yield 2,2-dimethyl-1-(3-phenoxybenzyloxy)-4,4-dichlorobut-3-ene (0.2 g).

$^1$H nmr (CDCl$_3$) ppm: 1.2 (s,6H); 3.25 (s,2H); 4.5 (s,2H); 6.0 (s,1H); and 6.9–7.4 (m, 9H).

Infra Red (liquid film): 1615, 1590, 1490, 1260, 1220, 1105, 880 and 695 cm$^{-1}$.

EXAMPLE 21

This Example illustrates the preparation of 2,2-dimethyl-1-(3-benzyl-4-fluorobenzyloxy)-4,4-dichlorobut-3-ene (Compound No 20).

A mixture of 2,2-dimethyl-3-(3-benzyl-4-fluoro-benzyloxy)propan-1-al (0.4 g), triphenylphosphine (0.77 g), zinc dust (0.10 g) and carbon tetrachloride (3 cm$^3$) in dichloromethane (3 ml) was heated at the reflux temperature for five hours. After cooling to the ambient temperature (ca 25° C.), the mixture was allowed to stand for 14 hours where upon it was triturated with diethylether. The solvent was evaporated under reduced pressure and the residue was passed through a short plug of silica gel using petroleum ether (boiling range 40°–60° C.) containing diethyl ether (10% by volume) as eluent to give 2,2-dimethyl-1-(3-benzyl-4-fluorobenzyloxy)-4,4-dichlorobut-3-ene (0.44 g).

$^1$H nmr (CDCl$_3$) ppm: 1.17 (s,6H); 3.23 (s,2H); 4.00 (s,2H); 4.43 (s,2H); 5.96 (s,1H); 6.95–7.3 (m,8H).

Infra Red (liquid film): 2890, 1618, 1505, 1150, 1400, 880 and 700 cm$^{-1}$.

GLC retention time: 9.37 minutes.

EXAMPLE 22

This Example illustrates the preparation of 1-(2,2-dichlorovinyl)-1-(3-phenoxybenzyloxymethyl)cyclopropane (Compound No 9).

A mixture of 1-formyl-1-(3-phenoxybenzyloxymethyl)cyclopropane (1 g), zinc dust (0.44 g), triphenylphosphine (1.78 g) and carbon tetrachloride (1.04 g) was heated at 60° C. for four hours. After cooling to the ambient temperature the mixture was diluted with petroleum ether (boiling range 40°–60° C.) and the solid component removed by filtration.

The filtrate was concentrated by evaporation of the solvent under reduced pressure and the residual oil subjected to purification by flash chromatography using a silica gel column eluted with dichloromethane, followed by h.p.l.c using a 40 cm long silica gel column with a 30 cm$^3$/min flow rate of hexane containing diethyl ether (27% by volume) as eluent to yield 1-(2,2-dichlorovinyl)-1-(3-phenoxybenzyloxymethyl)cyclopropane (0.236 g).

$^1$H nmr (CDCl$_3$) ppm: 0.75 (m,2H); 0.8 (m,2H); 3.4 (s,2H); 4.5 (s,2H); 6.05 (s,1H); and 6.9–7.4 (m,9H).

Infra Red (liquid film): 1590, 1490, 1260, 1220, 1105 and 695 cm$^{-1}$.

EXAMPLE 23

This Example illustrates the preparation of 2,2-dimethyl-1-(6-phenoxypyrid-2-yl)methoxy-4,4-dichlorobut-3-ene (Compound No 13).

2,2-Dimethyl-3-(6-phenoxypyrid-2-yl)methoxypropan-1-al was reacted according to the method illustrated in Example 22 to give 2,2-dimethyl-1-(6-phenoxypyrid-2-yl)methoxy-4,4-dichloro-but-3-ene.

$^1$H nmr (CDCl$_3$) ppm: 1.2 (s,6H); 3.4 (s,2H); 4.5 (s,2H); 6.0 (s,1H); 6.7 (d,1H); 7.2 (m,4H); 7.4 (t,2H); 7.7 (t,1H).

Infra Red (liquid film): 2950, 2870, 1610, 1595 and 1435 cm$^{-1}$.

GLC retention time: 8.44 minutes.

EXAMPLE 24

This Example illustrates the preparation of 2,2-dimethyl-1-(3-phenoxybenzyloxy)-4-chlorobut-3-ene (Compound No 10).

Chloromethyltriphenylphosphonium chloride (0.8 g) was added in portions to a stirred suspension of potassium t-butoxide (0.3 g) in dry tert-butanol (5 cm$^3$), and the resultant mixture was stirred for one hour after which a solution of 2,2-dimethyl-3-(3-phenoxybenzyloxy)propan-1-al (0.5 g) in tert-butanol (2 cm$^3$) was added.

After two hours, the reaction mixture was poured into water, and extracted with ethyl acetate, the extracts combined, washed with water and dried over anhydrous magnesium sulphate, and concentrated by evaporation of the solvent to yield an orange oil. This was flash chromatographed on a silica gel column using dichloromethane as eluent to yield 2,2-dimethyl-1-(3-phenoxybenzyloxy)-4-chlorobut-3-ene as a mixture of Z and E isomers (in the ratio of 2:1) by nmr spectroscopic and GLC examination (0.4 g).

$^1$H nmr (CDCl$_3$) ppm: 1.0 and 1.2 (s,6H); 3.2 and 3.35 (s,2H), 4.45 and 4.5 (s,2H); 5.7–5.95 (m,2H); and 6.9–7.4 (m,9H).

Infra Red (liquid film): 1590, 1260, 1220, 1105 and 695 cm$^{-1}$.

EXAMPLE 25

This Example illustrates the preparation of 2,2-dimethyl-1-(3-phenoxybenzyloxy)-4,4-dibromobut-3-ene (Compound No 3).

A solution of 2,2-dimethyl-3-(3-phenoxybenzyloxy)-propan-1-al (0.5 g) in dry dichloromethane (1.5 cm$^3$) was added to a preformed mixture of carbon tetrabromide (0.58 g) and triphenylphosphine (0.93 g) in dichloromethane (7.5 cm$^3$). The reaction mixture was stirred for two hours, whereupon it was diluted with more dichloromethane, and washed with water.

The organic layer was dried over anhydrous magnesium sulphate, and the solvent removed by evaporation. The residue was then subjected to purification by flash chromatography, using a silica gel column eluted with dichloromethane to yield 2,2-dimethyl-1-(3-phenoxybenzyloxy)-4,4-dibromobut-3-ene (0.12 g) as a colourless oil.

$^1$H nmr (CDCl$_3$) ppm: 1.2 (s,6H); 3.3 (s,2H); 4.5 (s,2H); 6.65 (s,1H); and 6.9–74 (9H).

Infra Red (liquid film) : 1590, 1490, 1260, 1105 and 690 cm$^{-1}$.

EXAMPLE 26

This Example illustrates the preparation of E-2,2-dimethyl-1-(3-phenoxybenzyloxy)-4-bromobut-3-ene (Compound No 7).

A mixture of 2,2-dimethyl-1-(3-phenoxybenzyloxy)-4,4-dibromobut-3-ene (0.2 g), diethylphosphite (0.15 g) and triethylamine (0.11 g) were stirred together at the ambient temperature (ca 24° C.) for six hours. The reaction mixture was then heated at 80° C. for three hours, and allowed to cool to the ambient temperature.

After dilution with diethyl ether, the solid component was removed by filtration and the filtrate was concentrated by evaporation of the solvent under reduced pressure. The residual oil was subjected to purification by flash chromatography using a silica gel column eluted with petroleum ether (boiling range 40°–60° C.) containing diethyl ether (10% by volume) to yield E-2,2-dimethyl-1-(3-phenoxybenzyloxy)-4-bromobut-3-ene (0.038 g).

$^1$H nmr (CDCl$_3$) ppm: 1.0 (s,6H); 3.2 (s,2H); 4.44 (s,2H); 6.05 (d,1H); 6.25 (d,1H); and 6.9–7.4 (m,9H).

Mass spectrum (m/e): 362 and 360 (m+), 251, 184 and 183.

EXAMPLE 27

This Example illustrates the preparation of Z,E-2,2-dimethyl-1-(3-phenoxybenzyloxy)-4-chloro-4-fluorobut-3-ene. (Compound No 11).

Dry methanol (0.04 g) was added portionwise to a stirred suspension of sodium hydride (0.034 g), triphenylphosphine (0.4 g) and methyl dichlorofluoroacetate (0.22 g) in hexane (1 ml). An effervescence and the formation of an orange suspension was noted. After a further thirty minutes, a solution of 2,2-dimethyl-1-(3-phenoxybenzyloxy)propan-1-al (0.4 g) in hexane (1 ml) was added and stirring was continued for four hours, after which time the reaction mixture was allowed to stand for a further sixteen hours. The reaction mixture was then poured into water, and extracted with ethyl acetate. The extracts were combined, washed with water, dried over anhydrous magnesium sulphate and concentrated by evaporation of the solvent to give a yellow solid, composed of the desired product, triphenyl phosphine, triphenyl phosphine oxide, and other by-products.

The crude product was subjected to flash chromotography on a silica gel column using dichloromethane as eluent to yield a product identified by nmr spectroscopy as a mixture of the desired product and triphenyl phosphine.

Meta-Chloroperbenzoic acid (0.1 g) was added to a solution of this impure product in dichloromethane (5 cm$^3$), and after stirring at the ambient temperature (ca 25° C.) for ten minutes the reaction mixture was washed with aqueous sodium bicarbonate solution, dried, and concentrated by evaporation of the solvent to yield a yellow solid which was subjected to purification by flash chromotograpy on a silica column using dichloromethane as eluent. The yellow isolated was distilled through a Kugelrohr apparatus (b.p 100° C. at 1 mm Hg) to yield 2,2-dimethyl-1-(3-phenoxybenzyloxy)-4-chloro-4-fluorobut-3-ene (0.074 g) identified as a 1:1 mixture of the E and Z isomers by nmr spectroscopic examination.

$^1$H nmr (CDCl$_3$) ppm: 1.15 (2s,6H); 3.2 (2s, 2H); 4.45 (s,2H); 4.87 (d,1H); 5.42 (d,1H); and 6.9–7.4 (m,9H).

$^{19}$F nmr (CDCl$_3$) ppm: −72.4 (d), −77.0 (d).

Infra Red (liquid film): 1590, 1490, 1260, 1100 and 700 cm$^{-1}$.

EXAMPLE 28

This Example illustrates the preparation of E,Z-2,2-dimethyl-1-(6-phenoxypyrid-2-yl)methoxy-4-chloro-4-fluorobut-3-ene (Compound No 19).

2,2-Dimethyl-3-(6-phenoxypyrid-2-yl)methoxypropan-1-al was reacted according to the method illustrated in Example 27 to give 2,2-dimethyl-1-(6-phenoxypyrid-2-yl)methoxy-4-chloro-4-fluorobut-3-ene as a mixture of isomers.

$^1$H nmr (CDCl$_3$) ppm: 1.18, 1.20 (2s,6H); 3.30, 3.34 (2s,2H); 4.53 (s,2H); 4.9, 5.48 (2d,1H);6.68 (d,1H); 7.14 (m,4H); 7.39 (t,2H); 7.68 (t,1H).

$^{19}$F nmr (CDCl$_3$) ppm: −72.4 and −76.4 (2d).

Infra Red (liquid film): 1665, 1600, 1580, 1495, 1450, 1440 and 700 cm$^{-1}$.

GLC retention time: 8.04 and 8.10 minutes.

EXAMPLE 29

This Example illustrates the preparation of 2,2-dimethyl-1-(4-fluoro-3-phenoxybenzyloxy)-4,4-difluorobut-3-ene (Compound No 15).

Hexamethylphosphorous triamide (0.65 g) was added portionwise to a stirred solution of dibromodifluoromethane (0.42 g) in triglyme (3 cm$^3$) whilst being maintained at 0° C. under an atmosphere of nitrogen. After a period of 10 minutes a pale yellow colouration was observed and a solution of 2,2-dimethyl-3-(4-fluoro-3-phenoxybenzyloxy)propan-1-al (0.3 g) in triglyme (2 cm$^3$) was added. After stirring for a further two hours, whilst being maintained at 0° C., the reaction mixture was allowed to warm to the ambient temperature. When GLC examination of a worked-up portion of the reaction mixture showed an absence of further reaction, the reaction mixture was poured into diethylether and sequentially washed with water and brine. The solvent was removed by evaporation under reduced pressure to give a pale yellow liquid which was subjected to short-path distillation (boiling point 75° C./0.01 mm Hg). The residue was then subjected to column chromatography on silica gel using petroleum ether (boiling range 40°–60° C.) containing 5% by volume diethyl ether as eluent to give 2,2-dimethyl-1-(4-fluoro-3-phenoxybenzyloxy)-4,4-difluorobut-3-ene (0.045 g).

$^1$H nmr (CDCl$_3$) ppm: 1.02 (s,6H); 3.10 (s,2H); 4.1 (dd,1H); 4.36 (s,2H); 6.8–7.3 (m,8H).

$^{19}$F nmr (CDCl$_3$) ppm: −86.63 (d); −86.84 (s); −133.33 (m).

Infra Red (liquid film): 2980, 2880, 1745, 1695, 1518, 1495, 1285, 1220, 820, 740 and 695 cm$^{-1}$.

EXAMPLE 30

The following compounds were prepared according to the procedure given in Example 29.

(I) 2,2-dimethyl-1-(6-phenoxypyrid-2-yl)methoxy-1,1-difluorobut-1-ene from 2,2-dimethyl-3-(6-phenoxypyrid-2-yl)methoxypropan-1-al (Compound No 16).

$^1$H nmr (CDCl$_3$) ppm: 1.1 (s,6H); 3.27 (s,2H); 4.22 (dd,1H); 4.5 (s,2H); 6.5–7.8 (m,8H).

$^{19}$F nmr (CDCl$_3$) ppm: −86.68 (d); −86.89 (s).

Infra Red (liquid film): 1745, 1600, 1580, 1500, 1450, 1440, and 700 cm$^{-1}$.

GLC retention line: 6.84 minutes.

(II) 2,2-dimethyl-3-(3-phenoxybenzyloxy)-1,1-difluorobut-1-ene from 2,2-dimethyl-3-(3-phenoxybenzyloxy)propan-1-al (Compound No 17).

$^1$H nmr (CDCl$_3$) ppm: 1.1 (s,6H); 3.20 (s,2H); 4.22 (dd,1H); 4.50 (s,2H); 6.9–7.125 (m,6H); 7.25–7.35 (m,3H).

$^{19}$F nmr (CDCl$_3$) ppm: −86.72 (d); −86.93 (s).

Infra Red (liquid film): 1745, 1590, 1490, 1260, 1220 and 700 cm$^{-1}$.

GLC retention time: 6.93 minutes.

(III) 2,2-dimethyl-3-(3-benzyl-4-fluorobenzyloxy)-1,1-difluorobut-1-ene from 2,2-dimethyl-3(3-benezyl-4-fluorobenzyloxy)propan-1-al (Compound No 18).

$^1$H nmr (CDCl$_3$) ppm: 1.1 (s,2H); 3.1 (s,2H); 3.9 (s,2H); 4.15 (dd,1H); 4.4 (s,2H); 6.8–7.2 (m,8H).

$^{19}$F nmr (CDCl$_3$) ppm: −86.74 (d); −86.95 (s); −120.38 (m).

Infra Red (liquid film): 1745, 1605, 1505, 1338, 1250, 1145, 1105, and 700cm$^{-1}$.

GLC retention time: 6.98 minutes.

EXAMPLE 31

This Example illustrates the insecticidal properties of the compound of this invention.

The activity of the compound was determined using a variety of insect pests. The compound was used in the form of liquid preparations containing 500 parts per million (ppm) by weight of the compound. The preparations were made by dissolving the compound in acetone and diluting the solutions with water containing 0.01% by weight of a wetting agent sold under the trade name "LISSAPOL" NX until the liquid preparations contained the required concentration of the compound. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species *Musca domestica* (housefly), additional tests to determine the knockdown effect of the compounds were performed. Details are given in Table II.

The results of the tests are given in Table III for each of the compounds, at the rate in parts per million given in the second column as a grading of mortality designated as A, B or C wherein A indicates 80–100% mortality or knockdown, B indicates 50–79% mortality or knockdown and C indicates less than 50% mortality or knockdown.

In Table III the pest organism used is designated by a letter code and the pests species, the support medium or food, and the type and duration of test is given in Table II.

TABLE II

| CODE LETTERS (Table IV) | TEST SPECIES | SUPPORT MEDIUM/FOOD | TYPE OF TEST | DURATION (days) |
|---|---|---|---|---|
| TU | *Tetranychus urticae* (red spider mites - adult) | French bean leaf | Contact | 3 |
| MP | *Myzus persicae* (aphids) | Leaf | Contact | 2 |
| NL | *Nilaparvata lugens* (green leaf hopper) | Cabbage leaf | Contact | 6 |
| HV | *Heliothis viriscens* (tobacco budworm) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| MD/KD | *Musca domestica* (houseflies - adults) | Cotton/wool sugar | Knockdown | 4 hours |
| CP | *Chilo partellurs* (Stem borers) | Oil seed rape leaf | Residual | 3 |

"Contact" test indicates that both pests and medium were treated and "residual" indicates that the medium was treated before infestation with the pests.

TABLE III

| Compound Number | Rate (ppm) | TU | MP | NL | MD KD | MD | BG | HV | CP | DB |
|---|---|---|---|---|---|---|---|---|---|---|
| 1 | 500 | — | C | A | A | A | A | A | A | A |
| 2 | 500 | — | C | A | A | A | C | C | — | A |
| 3 | 500 | — | C | B | C | C | C | C | A | C |
| 4 | 500 | C | C | A | A | C | C | C | — | C |
| 5 | 500 | A | A | A | A | A | A | C | — | A |
| 6 | 500 | C | C | B | C | C | C | C | C | C |
| 7 | 500 | C | C | B | C | C | C | C | C | C |
| 8 | 500 | A | C | A | A | A | C | C | — | A |
| 9 | 500 | C | A | A | A | A | B | C | — | B |
| 10 | 500 | C | C | A | A | B | C | — | C | A |
| 11 | 500 | C | C | A | A | B | B | B | — | A |
| 12 | 500 | C | C | A | A | C | C | C | — | A |
| 13 | 500 | C | B | A | A | B | A | A | — | A |
| 14 | 500 | C | C | A | A | A | B | C | — | A |
| 15 | 500 | A | A | A | A | A | A | A | — | A |
| 16 | 500 | A | A | A | A | — | A | A | — | A |
| 17 | 500 | C | C | A | A | — | A | C | — | A |
| 18 | 500 | B | C | A | A | — | A | A | — | A |
| 19 | 500 | B | B | A | A | — | B | C | — | A |
| 20 | 500 | C | C | A | C | — | C | C | — | C |

I claim:

1. A compound of formula:

$$CXY=CH-CR^1R^2-CH_2OCH_2R$$

wherein X and Y are each selected from hydrogen and halogen, $R^1$ and $R^2$ are each lower alkyl of up to four carbon atoms, or together with the adjacent carbon atom form a cycloalkyl group of up to six carbon atoms, and R represents a phenoxy- or benzyl-substituted phenyl group which may optionally be substituted with fluorine.

2. A compound according to claim 1 wherein X and Y are each selected from hydrogen, fluoro, chloro and bromo, $R^1$ and $R^2$ are methyl or ethyl or together represent the dimethylene group, and R is a group of formula:

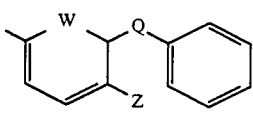

where W represents a carbon atom bearing a hydrogen atom, Z is hydrogen or fluoro, and Q is oxygen or methylene.

3. A compound according to claim 1 where R is selected from 3-phenoxyphenyl, 3-phenoxy-4-fluorophenyl, and 3-benzyl-4-fluorophenyl.

4. An insecticidal composition comprising an insecticially effective amount of a compound according to claim 1 in association with an insecticidally inert diluent or carrier material.

5. A method of combating insect pests at a locus which comprises treating the locus with an insecticidally effective amount of a composition according to claim 4.

* * * * *